| United States Patent [19] | [11] | 4,238,629 |
|---|---|---|
| Bauer et al. | [45] | Dec. 9, 1980 |

[54] PROCESS FOR THE PREPARATION OF A MIXTURE OF 2-AND 4-HYDROXYBENZYL ALCOHOL

[75] Inventors: Kurt Bauer; Reiner Mölleken, both of Holzminden; Karlfried Wedemeyer, Cologne; Helmut Fiege, Leverkusen, all of Fed. Rep. of Germany

[73] Assignee: Bayer Aktiengesellschaft, Leverkusen, Fed. Rep. of Germany

[21] Appl. No.: 71,428

[22] Filed: Aug. 30, 1979

[30] Foreign Application Priority Data

Apr. 14, 1979 [DE] Fed. Rep. of Germany ....... 2915216

[51] Int. Cl.³ .................... C07C 33/20; C07C 39/11
[52] U.S. Cl. .................................................. 568/764
[58] Field of Search ........................................ 569/764

[56] References Cited

U.S. PATENT DOCUMENTS 526,786  10/1894  Manasse ............................... 568/764

FOREIGN PATENT DOCUMENTS 994920  6/1965  United Kingdom ..................... 568/764

OTHER PUBLICATIONS

Riddick et al., "Organic Solvents", 3rd ed. (1970), Techniques of Chemistry, vol. II, pp. 6, 214.

Primary Examiner—Joseph E. Evans
Attorney, Agent, or Firm—Sprung, Felfe, Horn, Lynch & Kramer

[57] ABSTRACT

Mixtures of 2- and 4-hydroxybenzyl alcohol with high contents of 4-hydroxybenzyl alcohol are obtained by a process comprising reacting phenol and paraformaldehyde in the presence of a strongly basic catalyst and a polyalkylene polyether.

4 Claims, No Drawings

PROCESS FOR THE PREPARATION OF A MIXTURE OF 2- AND 4-HYDROXYBENZYL ALCOHOL

The invention relates to a process for the preparation of a mixture of 2- and 4-hydroxybenzyl alcohol.

A process for the preparation of mixtures of 2- and 4-hydroxybenzyl alcohol is described in DE-OS (German Published Specification) No. 2,729,075. In this process, the mixtures are obtained in high space/time yields by reaction of phenol and paraformaldehyde in the presence of strongly basic catalysts. However, the proportion of 4-hydroxybenzyl alcohol in these mixtures is only about 30% by weight, relative to the hydroxybenzyl alcohols present in the reaction mixture.

Since 4-hydroxybenzyl alcohol is an important starting material for the preparation of 4-hydroxybenzaldehyde, there was a need to prepare mixtures of 2- and 4-hydroxybenzyl alcohol containing a higher proportion of 4-hydroxybenzyl alcohol.

It has been found, surprisingly, that the proportion of 4-hydroxybenzyl alcohol in the said hydroxybenzyl alcohol mixtures can be increased considerably if the reaction of phenol and paraformaldehyde is carried out using strongly basic catalysts in the presence of polyalkylene polyethers.

The invention thus relates to a process for the preparation of mixtures of 2- and 4-hydroxybenzyl alcohol by reaction of phenol and paraformaldehyde in the presence of strongly basic catalysts, which is characterised in that the reaction is carried out in the presence of polyalkylene polyethers.

The polyalkylene polyethers advantageously have a molecular weight of about 140 to 14,000. They can be open-chained or cyclic ethers.

Examples of open-chained polyalkylene polyethers which may be mentioned are: polyalkylene glycols and monoethers and diethers thereof, for example polyethylene glycols, polypropylene glycols, mixed polyethylene/propylene glycols and alkyl, aralkyl and aryl ethers thereof, for example methyl, ethyl, propyl, butyl, pentyl, hexyl, benzyl, phenyl and $C_1$–$C_{12}$-alkyl-phenyl ethers.

Examples of representatives which may be mentioned are polyethylene glycols with molecular weights of 1,500, 3,600 and 12,000, triethylene glycol monomethyl ether, polyethylene glycol dimethyl ether and tetraethylene glycol monoethyl ether; polypropylene glycols with molecular weights of 400–5,000; and octylphenol, nonylphenol or dodecylphenol which has been reacted with 16 to 24 mols of ethylene oxide per mol of phenol.

Examples of cyclic polyethers which may be mentioned are the cyclic polyethers with an average to large number of members, called "crown ethers", in which the ether oxygen atoms are bonded by alkylene bridges, preferably ethylene bridges, and which can contain one or more fused benzene, cyclohexane or hetero-aromatic rings (see J. Am. Chem. Soc. 89, 7,017 (1967); Chem. Rev. 74, 354 (1974) and Chem. Commun. 1976; 295). Examples of representatives of the crown ethers which may be mentioned are: 1,4,7,10-tetraoxacyclododecane (12-crown-4), 1,4,7,10,13-pentaoxacyclopentadecane (15-crown-5), 1,4,7,10,13,16-hexaoxacyclooctadecane (18-crown-6), 2,5,8,15,18,21-hexaoxatricyclo[20,4,0,0$^{9,14}$]hexacosane (dicyclohexyl-18-crown-6), 1,4,7,14,23-pentaoxa[7,2]orthocyclo[2](2,6)-pyridinophane (dibenzopyridino-18-crown-6) and 1,13-bis-(8-quinolyl)-1,4,7,10,13-pentaoxatridecane.

The polyalkylene polyethers to be used according to the invention are employed in an amount of 0.05 to 10 g, preferably 0.1 to 5 g, per mol of phenol.

Sodium hydroxide and potassium hydroxide are preferably used as the strongly basic catalysts in the process according to the invention. The catalysts are employed in an amount of 0.0001 to 0.05 mol, preferably 0.0005 to 0.02 mol, per mol of phenol.

Phenol and paraformaldehyde are employed in a molar ratio of 5–15:1, preferably 8–21:1, in the process according to the invention.

The polyalkylene polyethers and strongly basic catalyst can be added to the reaction components at the start of the reaction. However, in some cases it has proved advantageous not to add the strongly basic catalyst all at once at the start of the reaction, as is the case with the polyalkylene polyethers, but to add only one third of the total amount of catalyst at the start of the reaction and to add the remaining two thirds in the course of the reaction.

The process according to the invention is advantageously carried out at temperatures of 25° to 120° C., preferably 40° to 90° C. The reaction time varies between 0.5 and 6 hours.

The reaction mixture can be worked up, as described in DE-OS (German Published Specification) No. 2,729,075, by distilling off some of the excess phenol and isolating the 2- and 4-hydroxybenzyl alcohols by counter-current extraction.

EXAMPLE 1

1.25 mols of phenol and 0.125 mol of paraformaldehyde (water content: 3.6% by weight) are warmed to 65° C., whilst stirring. After adding 0.08 g of 50% strength aqueous potassium hydroxide (0.0007 mol) and 0.75 g of polyethylene glycol (molecular weight: 400), the reaction mixture is kept at 65° C. for 4 hours. A further 0.16 g of 50% strength aqueous potassium hydroxide (0.0014 mol) is then added and the reaction is brought to completion by stirring the mixture at 65° C. for 2 hours.

The potassium hydroxide is then neutralized with an equivalent amount of acetic acid and some of the excess phenol is distilled off, first in a falling film evaporator and then in a thin film evaporator, at 55° to 60° C. and under 3 to 5 mm Hg.

The proportions of 2- and 4-hydroxybenzyl alcohol in the reaction mixture thus obtained are determined by high pressure liquid chromatography, or, after acetylating the reaction mixture, by gas chromatography. The reaction mixture contains 53.4% of 2-hydroxybenzyl alcohol and 46.6% of 4-hydroxybenzyl alcohol (relative to the total amount of hydroxybenzyl alcohols in the reaction mixture).

EXAMPLES 2 to 13

1.25 g of phenol and 0.125 mol of paraformaldehyde (water content: 3.6% by weight) were reacted at 65° C. for 6 hours in the manner described in Example 1, using the amount of 50% strength aqueous potassium hydroxide indicated in Table 1 and in the presence of the polyalkylene polyethers indicated in Table 1.

Analysis of the hydroxybenzyl alcohol mixtures obtained in these reactions gave the contents of 2- and 4-hydroxybenzyl alcohol indicated in Table 1 (all relative to the total content of hydroxybenzyl alcohol in the reaction mixtures).

TABLE 1

| Example | Phenol [mol] | KOH (50% strength) [mol] | KOH (50% strength) [g] | Polyalkylene polyether [g] | 2-Hydroxybenzyl alcohol [%] | 4-Hydroxybenzyl alcohol [%] |
|---|---|---|---|---|---|---|
| 2 | 1.25 | 0.002 | 0.22 | Polyethylene glycol (MW 1,500) 0.75 | 56.8 | 43.2 |
| 3 | 1.25 | 0.002 | 0.22 | Polyethylene glycol (MW 12,000) 0.75 | 57.0 | 43.0 |
| 4 | 1.25 | 0.002 | 0.22 | Polypropylene glycol (MW 3,600) 0.75 | 60.7 | 39.3 |
| 5 | 1.25 | 0.002 | 0.22 | Polyethylene glycol monononylphenyl ether (MW 2,100) 0.75 | 58.8 | 41.2 |
| 6 | 1.25 | 0.002 | 0.22 | Triethylene glycol monomethyl ether 0.75 | 57.6 | 42.4 |
| 7 | 1.25 | 0.002 | 0.22 | Polyethylene glycol dimethyl ether (MW 200) 0.75 | 55.3 | 44.7 |
| 8 | 5 | 0.003 | 0.34 | Polyethylene glycol dimethyl ether (MW 200) 2.0 | 59.9 | 40.1 |
| 9 | 5 | 0.003 | 0.34 | Polyethylene glycol dimethyl ether (MW 200) 5.0 | 55.1 | 44.9 |
| 10 | 1.25 | 0.002 | 0.22 | [12] Crown-4 ether 0.75 | 56.3 | 43.7 |
| 11 | 1.25 | 0.002 | 0.22 | [15] Crown-5 ether 0.75 | 53.3 | 46.7 |
| 12 | 5 | 0.008 | 0.9 | [18] Crown-6 ether 1.3 | 51.0 | 49.0 |
| 13 | 5 | 0.008 | 0.9 | [18] Crown-6 ether 1.13 | 53.1 | 46.9 |

EXAMPLES 14 to 20

1.25 mols of phenol and 0.125 mol of paraformaldehyde (water content: 3.6% by weight) were reacted at 65° C. for 6 hours in the manner described in Example 1, using the strongly basic catalyst indicated in Table 2 and in the presence of the polyalkylene polyethers indicated in Table 2, with the modification that the entire amount of catalyst was added at the start of the reaction.

Analysis of the hydroxybenzyl alcohol mixtures obtained in these reactions gave the contents of 2- and 4-hydroxybenzyl alcohol indicated in Table 2 (relative to the total content of hydroxybenzyl alcohol in the reaction mixture).

What is claimed is:

1. In the known process for the preparation of a mixture of 2- and 4-hydroxybenzyl alcohol by reacting phenol and paraformaldehyde in the presence of strongly basic catalyst, the improvement comprising carrying out the reaction in the presence of a polyalkylene polyether having a molecular weight of 140 to 14,000, 0.05 to 10 g of polyalkylene polyether being used per mol of phenol.

2. The process according to claim 1, wherein the polyalkylene polyether is used in an amount of 0.1 to 5 g per mol of phenol.

3. The process according to claim 1, wherein the polyalkylene polyether is a polyalkylene glycol, a monoether or diether thereof and/or crown ether.

4. The process according to claim 1, wherein the polyalkylene polyether is a polyethylene glycol, a monoether or diether thereof.

TABLE 2

| Example | Phenol [mol] | Catalyst [mol] | Catalyst [g] | Polyalkylene polyether [g] | 2-Hydroxybenzyl alcohol [%] | 4-Hydroxybenzyl alcohol [%] |
|---|---|---|---|---|---|---|
| 14 | 5 | KOH (50% strength) 0.008 | 0.9 | Polyethylene glycol dimethyl ether (MW 200) 5 | 58.2 | 41.8 |
| 15 | 5 | NaOH 0.02 | 0.76 | [15] Crown-5 ether 4 | 54.8 | 45.2 |
| 16 | 5 | KOH (50% strength) 0.008 | 0.9 | [18] Crown-6 ether 1.0 | 62.0 | 38.0 |
| 17 | 5 | KOH (50% strength) 0.008 | 0.9 | [18] Crown-6 ether 1.3 | 62.0 | 38.0 |
| 18 | 5 | KOH (50% strength) 0.0035 | 0.4 | Dibenzo-[18] crown-6 ether 1.8 | 52.8 | 47.2 |
| 19 | 5 | KOH (50% strength) 0.035 | 0.4 | Dicyclohexyl-[18] crown-6 ether 1.8 | 54.1 | 45.9 |
| 20 | 5 | KOH (50% strength) 0.0035 | 0.4 | Dibenzopyridino-[18] crown-6 ether 1.9 | 54.4 | 45.6 |
| Comparison Example | 5 | KOH (50% strength) 0.01 | 1.2 | — | 70.0 | 30.0 |

* * * * *

UNITED STATES PATENT AND TRADEMARK OFFICE
CERTIFICATE OF CORRECTION

PATENT NO. : 4,238,629
DATED : Dec. 9, 1980
INVENTOR(S) : Kurt Bauer et al

It is certified that error appears in the above—identified patent and that said Letters Patent is hereby corrected as shown below:

Title Page, "Bayer Aktiengesellschaft, Leverkusen, Germany"
Assignee should be "Haarman & Reimer, GmbH, Holzminden, Germany"

Signed and Sealed this

Fifteenth Day of September 1981

[SEAL]

Attest:

GERALD J. MOSSINGHOFF

Attesting Officer    Commissioner of Patents and Trademarks